(12) United States Patent
Perrow

(10) Patent No.: US 11,540,867 B2
(45) Date of Patent: Jan. 3, 2023

(54) DRIVER FOR A BONE SCREW

(71) Applicant: Pioneer Surgical Technology, Inc., Marquette, MI (US)

(72) Inventor: Scott J. Perrow, Ishpeming, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 66 days.

(21) Appl. No.: 16/991,760

(22) Filed: Aug. 12, 2020

(65) Prior Publication Data

US 2021/0045791 A1  Feb. 18, 2021

Related U.S. Application Data

(60) Provisional application No. 62/886,092, filed on Aug. 13, 2019.

(51) Int. Cl.

| *A61B 17/58* | (2006.01) |
| *A61B 17/60* | (2006.01) |
| *A61F 2/00* | (2006.01) |
| *A61B 17/88* | (2006.01) |
| *A61B 17/86* | (2006.01) |
| *A61B 17/00* | (2006.01) |

(52) U.S. Cl.
CPC ...... *A61B 17/8888* (2013.01); *A61B 17/8615* (2013.01); *A61B 2017/00477* (2013.01)

(58) Field of Classification Search
CPC combination set(s) only.
See application file for complete search history.

(56) References Cited

U.S. PATENT DOCUMENTS

| 6,286,401 B1 | 9/2001 | Hajianpour |
| 7,226,453 B2 | 6/2007 | Chao |
| 7,452,361 B2 | 11/2008 | Kreidler |
| 7,909,834 B2 | 3/2011 | Selover |
| 8,808,307 B2 | 8/2014 | Robinson |
| 8,932,303 B2 | 1/2015 | Bouliane |
| 10,278,738 B2 | 5/2019 | Jackson |
| 2008/0215061 A1 | 9/2008 | Schumacher |

(Continued)

FOREIGN PATENT DOCUMENTS

| BR | PI0715176 A2 | 6/2013 |
| EP | 2691040 B1 | 2/2014 |

(Continued)

OTHER PUBLICATIONS

U.S. Appl. No. 62/886,092, filed Aug. 13, 2019 (30 pages).

*Primary Examiner* — Sameh R Boles
(74) *Attorney, Agent, or Firm* — Fitch, Even, Tabin & Flannery LLP

(57) ABSTRACT

In accordance to one aspect of the present disclosure, a driver for a bone screw is provided that includes an inner shaft and a distal drive head of the inner shaft. The drive head is configured to fit in a drive recess of a bone screw to form a mating connection therewith. The driver further includes at least one outer, resilient locking member shiftable along the inner shaft from a proximal, unlocked position to a distal, locked position. The resilient locking member has a locking portion that contacts and is urged outwardly by a proximal ramp surface of the drive head as the locking member shifts distally from the unlocked position to the locked position to secure the bone screw onto the drive head.

11 Claims, 8 Drawing Sheets

(56) References Cited

U.S. PATENT DOCUMENTS

2013/0150864 A1  6/2013  Marik
2015/0238236 A1  8/2015  Sasing
2018/0235684 A1* 8/2018  Hawkes ................ B25B 23/108

FOREIGN PATENT DOCUMENTS

ES   2356892 T3   4/2011
KR   101880424 A  2/2014

* cited by examiner

DRIVER FOR A BONE SCREW

CROSS-REFERENCE TO RELATED APPLICATION

This application claims the benefit of U.S. Provisional Patent Application No. 62/886,092, filed Aug. 13, 2019, which is hereby incorporated by reference in its entirety.

FIELD

This disclosure relates to a driver for surgical devices and, more particularly, to a driver for a bone screw.

BACKGROUND

Bone plate systems are often used to stabilize vertebrae. Bone plate systems typically include a bone plate and one or more through openings that receive bone screws. Bone screws typically have a head that receives a driver and a threaded shank. During implantation of the bone plate, the bone plate is positioned against vertebrae and holes are formed in the vertebrae aligned with the through openings of the bone plate. The bone plate may be held in place on the vertebrae using pins and the holes may be tapped in some applications.

The surgeon grasps a handle of a driver, connects a distal end of the driver to a bone screw, and manipulates the handle to advance the shank of the bone screw into one of the through openings of the bone plate and into the associated hole in a verterba. The surgeon may utilize a guide to direct the bone screw into the through opening, such as by advancing the screw through a cannula of a tubular guide connected to the bone plate. Alternatively, the surgeon may utilize a freehand approach whereby the surgeon maneuvers the bone screw into the through opening of the bone plate without a guide. The freehand approach may provide the surgeon with greater flexibility in selecting the insertion angle of the bone screw. The surgeon turns the handle of the driver to screw the bone screw into the vertebra. The surgeon repeats the process with other bone screws until the bone plate is secured to the vertebrae.

Drivers often have a retention mechanism for retaining a bone screw on the distal end of the driver. However, bone screws for smaller bones, such as cervical vertebrae, are often very small. For example, the head of a bone screw used in a cervical bone plate may only have an outer diameter of 4 millimeters and the length of the bone screw may only be approximately 12 millimeters. The small size of the bone screw head makes it difficult for the retention mechanism of a driver to adequately engage the bone screw head to secure the bone screw thereon. This issue is magnified when a surgeon elects to utilize a freehand technique because the bone screw may contact tissue or boney structures as the bone screw is advanced into the bone plate through opening. Additionally, some retention mechanisms utilize a drive element that expands in the drive recess of a bone screw to secure the bone screw to the driver. The drive element may be limited in the amount of torque the drive element may apply to the bone screw because a higher torque may contract the drive element and permit the bone screw to disengage from the drive element.

SUMMARY

In accordance with one aspect of the present disclosure, a driver for a bone screw is provided that includes an inner shaft and a distal drive head of the inner shaft. The drive head is configured to fit in a drive recess of a bone screw to form a mating connection therewith. The driver further includes at least one outer, resilient locking member shiftable along the inner shaft from a proximal, unlocked position to a distal, locked position. The resilient locking member has a locking portion that contacts and is urged outwardly by a proximal ramp surface of the drive head as the locking member shifts distally from the unlocked position to the locked position to secure the bone screw on the drive head. In this manner, the proximal ramp surface of the drive head translates the shifting of the resilient locking member along the inner shaft into outward movement of the locking portion of the resilient locking member so that the locking portion may engage the bone screw. The outward urging of the locking portion of the resilient locking member away from the distal drive head of the inner shaft imparts an expansion force on the bone screw that retains the bone screw on the driver. Further, the proximal ramp surface of the drive head provides a compact arrangement for redirecting the resilient locking member into engagement with a bone screw that fits in a drive recess of a small bone screw, such as a bone screw having a head diameter in the range of 3 mm to 6 mm.

In accordance with another aspect of the present disclosure, a bone screw driving system is provided that includes a bone screw and a driver. The driver includes an elongate shaft assembly having a proximal end portion, a distal end portion configured to connect to the bone screw, and a longitudinal axis extending therebetween. The distal end portion of the driver elongate shaft assembly includes an inner drive member configured to extend into a drive recess of the bone screw. The inner drive member further includes a distal surface configured to seat against the seating surface of the drive recess.

The distal end portion of the driver elongate shaft assembly further includes an outer expansion locking member spaced proximally from the distal surface of the drive member along the longitudinal axis. The outer expansion locking member has an initial configuration wherein the outer expansion locking member is proximal of the inner drive member distal surface and the outer expansion locking member permits the inner drive member to be advanced into the drive recess of the bone screw. The outer expansion locking member further has an expanded configuration wherein the outer expansion locking member is proximal of the inner drive distal surface and extends laterally outward of the inner drive member to engage the bone screw and fix the bone screw to the distal end portion of the driver elongate shaft assembly. In the expanded configuration, the outer expansion locking member projects laterally to create an interference with the bone screw and resist axial separation of the bone screw from the inner drive member. Because the outer expansion locking member is proximal of the inner drive member distal surface when in the initial and expanded configurations, the outer expansion locking member avoids limiting engagement between the distal end of the inner drive member and the drive recess. For example, the torque the inner drive member may apply to the bone screw is set by the materials and geometry of the inner drive member and the bone screw rather than being limited by presence of the outer expansion locking member.

The present disclosure also provides a method of connecting a driver to a bone screw. The method includes advancing an inner drive member of a distal end portion of an elongate shaft assembly of the driver into a drive recess of a bone screw. The method further includes positioning a ramp surface of the inner drive member adjacent to an undercut of the bone screw drive recess and shifting an outer locking portion of the driver elongate shaft assembly distal end portion distally along the inner drive member. The method further includes urging the outer locking portion outward into the undercut by engaging the outer locking portion with the ramp surface of the inner drive member as the outer locking portion shifts distally along the inner drive member. This locks the bone screw to the distal end portion of the driver elongate shaft. The method thereby permits the driver to be rapidly and securely connected to the bone screw so that the bone screw may be subsequently driven into bone.

DETAILED DESCRIPTION

Figure 1:
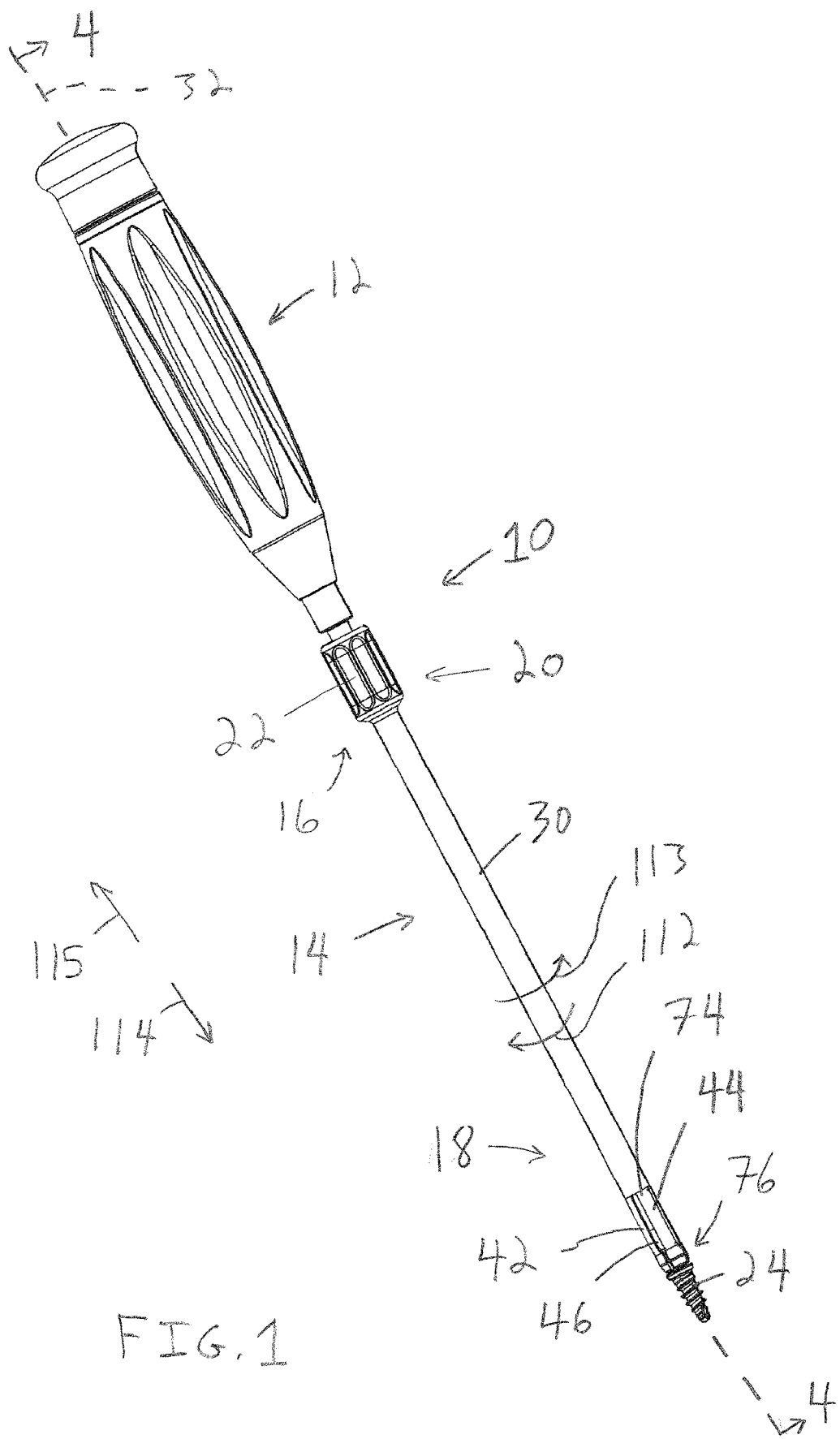
FIG. 1 is a perspective view of a driver and a bone screw showing a distal end portion of an elongate shaft of the driver secured to the bone screw.

With reference to FIG. 1, a driver 10 is provided that includes a handle 12, a shaft assembly 14, and a longitudinal axis 32. The shaft assembly 14 includes a proximal end portion 16 and a distal end portion 18. The driver 10 includes an actuator 20, such as a knob 22, operable to shift the distal end portion 18 from a release or unlocked configuration (see FIG. 5) wherein the distal end portion 18 may be connected to a bone screw 24 to a retention or locked configuration (see FIG. 8) wherein the distal end portion 18 is fixed to the bone screw 24. Regarding FIGS. 1 and 2, the shaft assembly 14 includes an outer sleeve 30 and an inner shaft 34. The actuator 20 shifts the outer sleeve 30 in distal direction 114 to reconfigure the distal end portion 18 from the unlocked to the locked configuration and in proximal direction 115 to reconfigure the distal end portion 18 from the locked to the unlocked configuration. In one embodiment, the outer sleeve 30 includes a sleeve portion 40 and an outer expansion locking member, such as one or more resilient locking members 42. The sleeve portion 40 and resilient locking members 42 are connected, such as by being assembled or by having a unitary, one-piece construction. In one embodiment, the resilient locking members 42 include arms 44 separated by openings such as elongate slots 46. The inner shaft 34 includes a tapered portion 50, a neck portion 52, and a drive member such as a drive head 54. The drive head 54 laterally expands the free ends of the arms 44 as the arms 44 are shifted in distal direction 114 onto the drive head 54 and causes the arms 44 to engage the bone screw 24. Conversely, the resiliency of the arms 44 laterally contracts the free ends of the arms 44 as the arms 44 are shifted in proximal direction 115 off of the drive head 54 and causes the arms 44 to disengage the bone screw 24. In one embodiment, the distal end portion 18 and bone screw 24 have generally circular configurations such that the lateral expansion and contraction is radial in nature.

Figure 3:
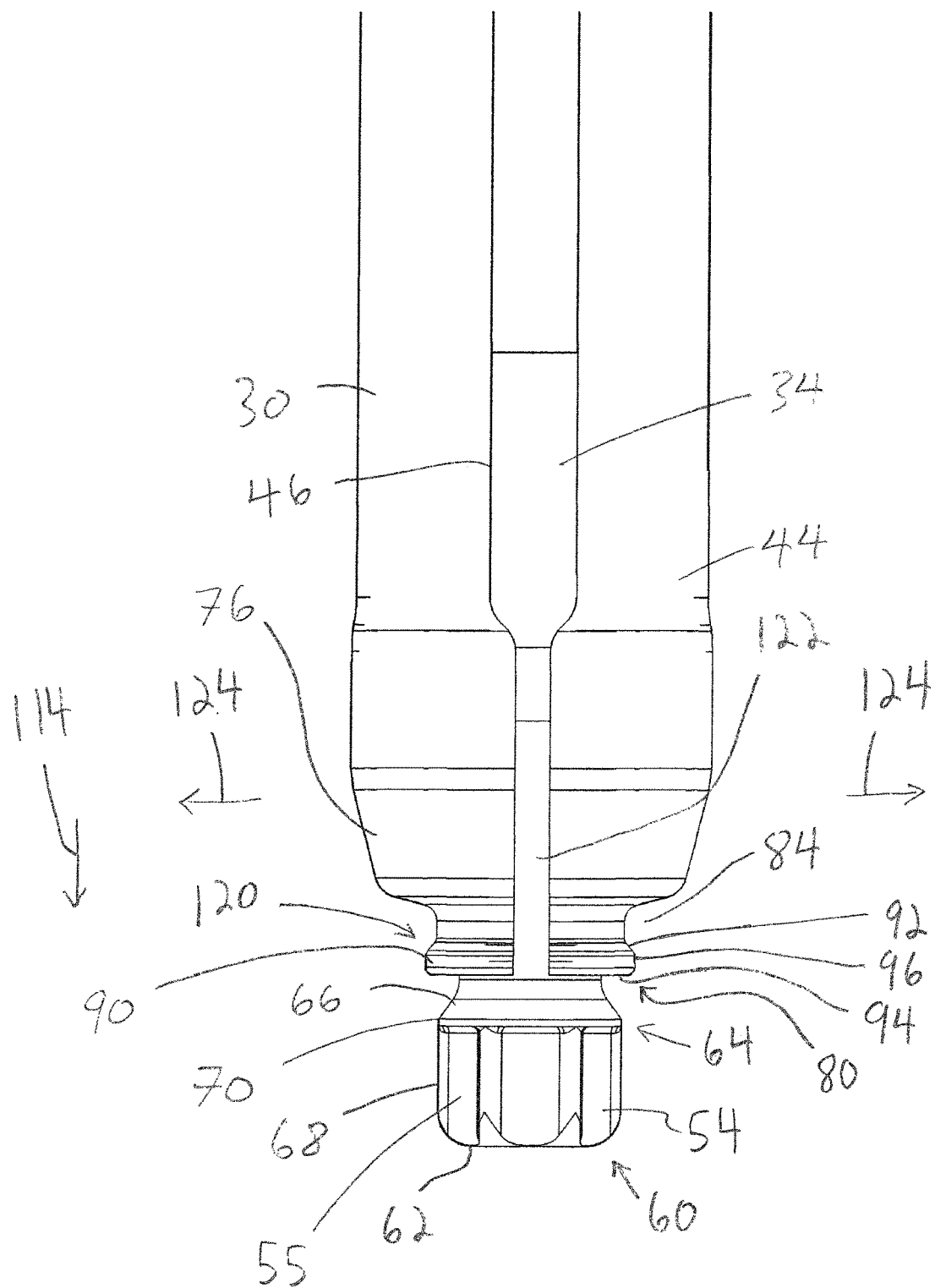
FIG. 3 is an elevational view of the distal end portion of the driver elongate shaft showing locking portions of the arms of the outer sleeve spaced proximally from a proximal ramp surface of the drive head.

More particularly and regarding FIG. 3, the drive head 54 of the inner shaft 34 includes a distal end portion 60 having a distal surface 62 and a proximal end portion 64 including a ramp surface 66. In one embodiment, the ramp surface 66 is annular and extends around the drive head 54. The drive head 54 includes one or more axially extending side surfaces 68 extending between the distal surface 62 and the ramp surface 66. Further, the drive head 54 includes a juncture 70 between the ramp surface 66 and the side surfaces 68. The side surfaces 68 may have projections and recesses to provide a predetermined cross-sectional profile for the drive head 54. For example, the drive head 54 may have hexagonal, tri-lobed, hex-lobed, or torx configurations as some examples.

Figure 8:
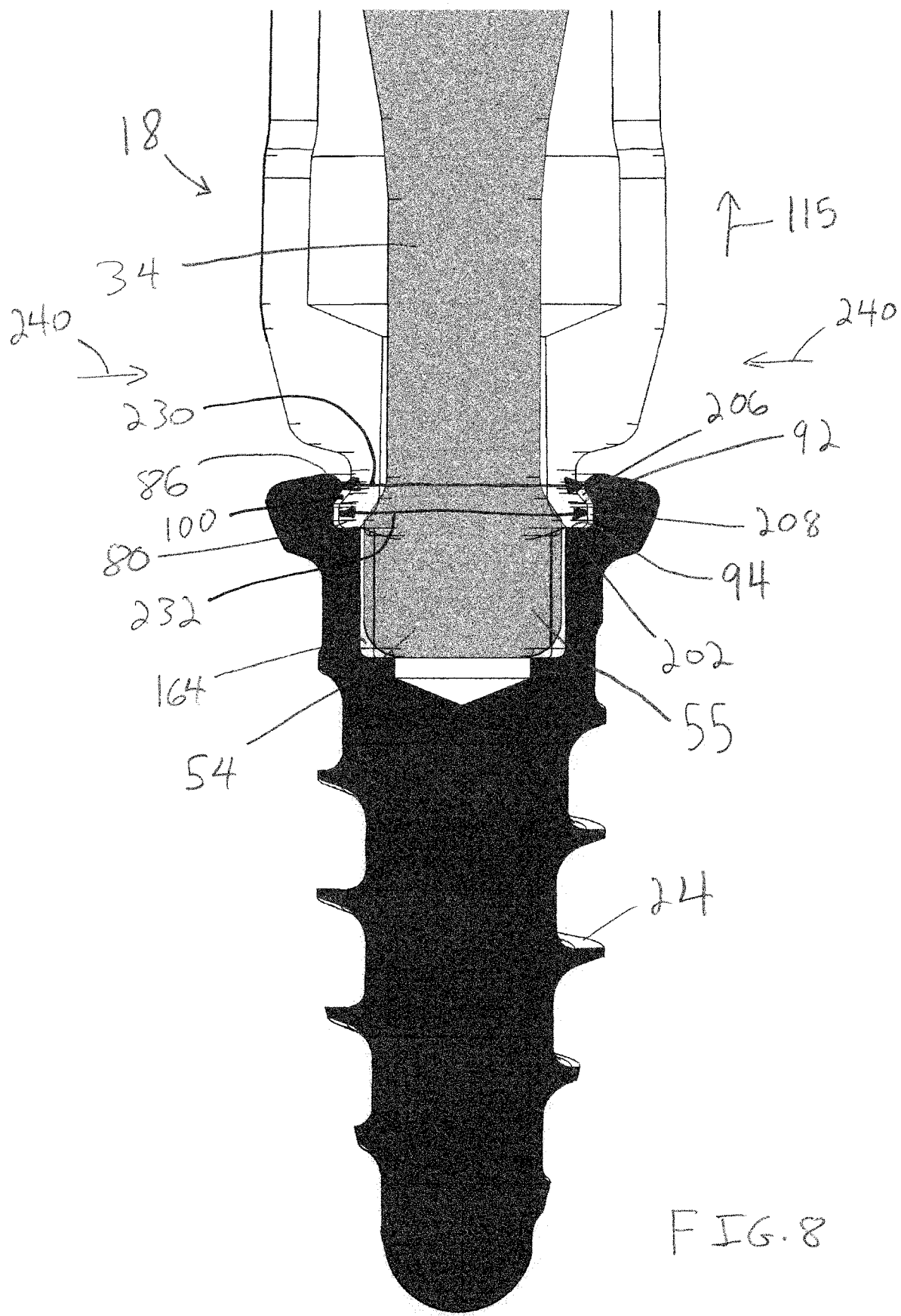
FIG. 8 is a cross-sectional view similar to FIG. 7 showing the shaft distal end portion in a locked configuration with the locking portions of the resilient arms extending into an undercut of the bone screw head portion which secures the bone screw to the driver shaft distal end portion.

As shown in FIGS. 3 and 8, a portion 55 of the drive head 54 below the juncture 70 is exposed for engagement with the drive structure of the bone screw 24 when the outer sleeve 30 is in an unlocked position (FIG. 3) or a locked position (FIG. 8). Further, the distal end portion 18 may engage the bone screw 24 without deforming or deflecting the drive head 54. The drive head 54 may thereby be made of a sufficiently rigid material with a geometry that permits the exposed drive head portion 55 to provide a desired torque to the bone screw 24. In one embodiment, the inner shaft 34 and drive head 54 thereof have a unitary, one-piece construction with the drive head 54 being solid. The side surfaces 68 of the solid drive head 54 directly transfer torque applied to the inner shaft 34 by the handle 12 to the drive structure of the bone screw 24 without the rigidity of the drive head 54 being limited by the engagement between the arms 44 and the bone screw 24.

In one embodiment, the bone screw 24 has a head portion 160 (see FIG. 5) that is rigid. The head portion 160 does not deform when the drive head 54 is seated in a drive recess 164 of the bone screw 24. Further, the head portion 160 does not deform when the outer sleeve 30 is shifted to the locked position and locking portions 80 of the arms 44 are urged radially outward into engagement with an undercut 100 of the bone screw 24 (see FIG. 8). The term "does not deform" is intended to encompass some minor deformation that does not substantively effect the resulting tolerances and engagement between the components. Unlike the bone screw head portion 160, the arms 44 resiliently deflect as the locking portions 80 are urged radially outward. The arms 44 apply a resilient bias force against the rigid head portion 160 of the bone screw 24, which tightly fixes the locking portions 80 in the undercut 100 of the bone screw 24 and fixes the bone screw 24 on the driver 10. In one embodiment, the outer sleeve 30 and inner shaft 34 are made of a metallic material, such as stainless steel, and the bone screw 24 is made of a metallic material, such as titanium. In another embodiment, the outer sleeve 30 and inner shaft 34 may be made of a plastic material. The outer sleeve 30 and inner shaft 34 may be made of the same or different materials.

Regarding FIGS. 1 and 3, the arms 44 include base portions 74 and free end portions 76. At the free end portions 76, the arms 44 each include a locking portion 80 configured to engage a retaining structure 82 (see FIG. 5) of the bone screw 24. The free ends 76 each include a groove 84 that receives a flange 86 (see FIG. 5) of the bone screw 24 and the locking portion 80 distal of the groove 84. The locking portion 80 may include a lip 90 having an upper locking surface 92, a lower leading surface 94, and an axial extending surface 96 extending therebetween. The lip 90 is configured to fit tightly in and engage the undercut 100 (see FIG. 5) of the bone screw 24. The lip 90 and undercut 100 have mating profiles that inhibit toggling or tilting of the bone screw 24 relative to the inner shaft 34. The actuator 20 holds the outer sleeve 30 in the locked position which maintains the rigid connection of the bone screw 24 on the distal end portion 18 of the driver 10. Further, with the lip 90 engaged in the undercut 100, the lip 90 is in axial overlapping relation below the flange 86 which inhibits axial movement of the bone screw 24 off of the inner shaft 34.

Figure 2:
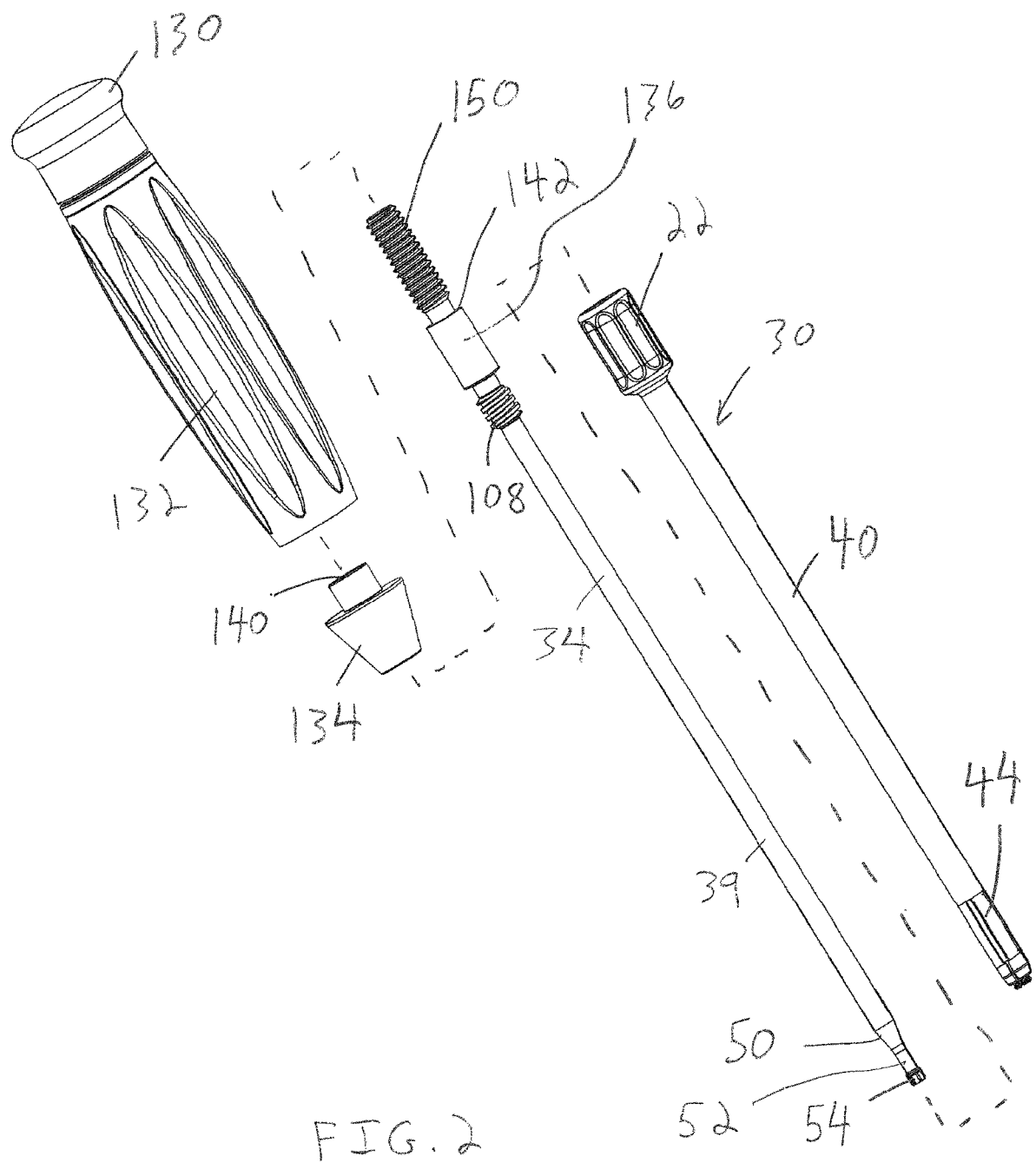
FIG. 2 is an exploded view of the driver of FIG. 1 showing an inner shaft having a drive head at a distal end thereof and an outer sleeve with resilient arms at a distal end thereof which are urged radially outwardly by a ramp surface of the drive head.
Figure 4:
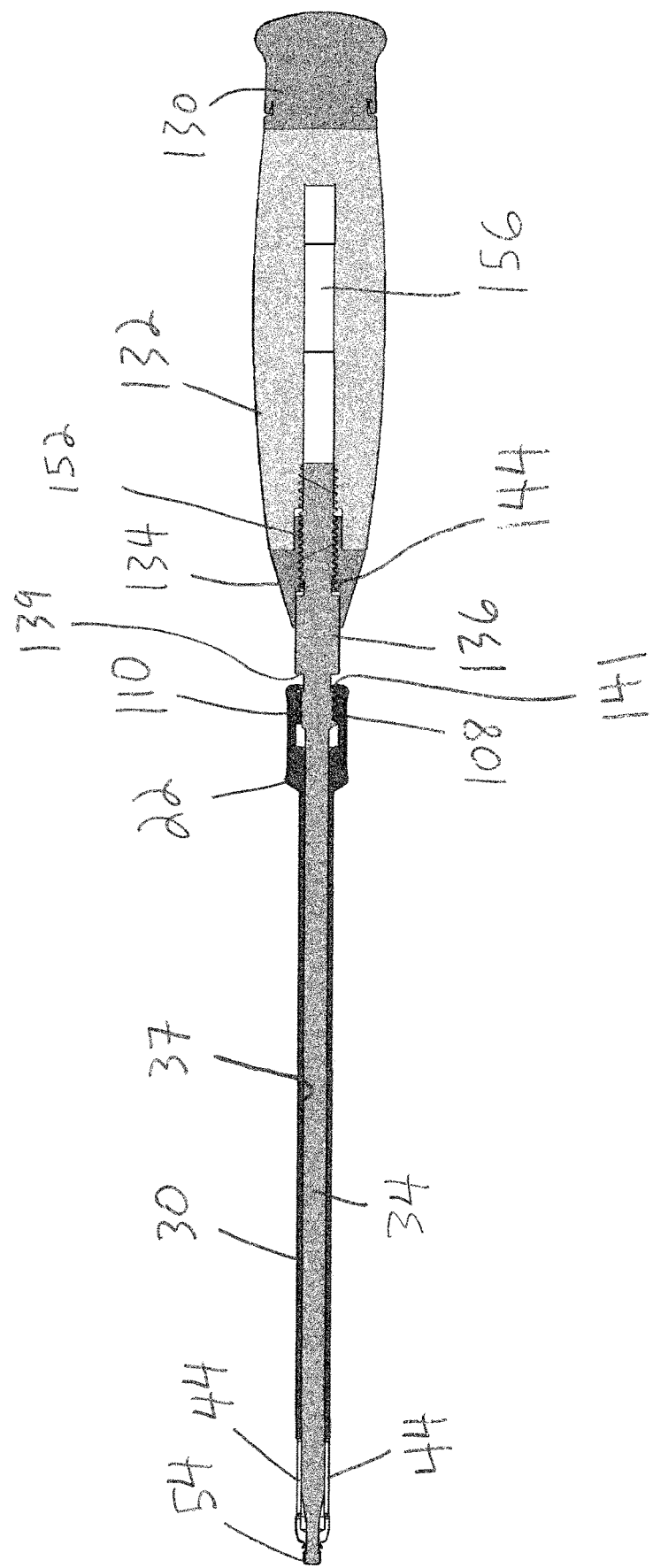
FIG. 4 is a cross-sectional view taken across line 4-4 in FIG. 1 showing a threaded connection between a knob of the outer sleeve and the inner shaft that permits the outer sleeve to be rotatably advanced distally to lock the arms to the bone screw and rotatably advanced proximally to release the arms from the bone screw.

Regarding FIGS. 2 and 4, in one embodiment the inner shaft 34 and the outer sleeve 30 have a rotatable connection therebetween that permits the outer sleeve 30 to turn relative to the inner shaft 34. The rotatable connection may permit the outer sleeve 30 to be shifted from the unlocked position to the locked position with less than 360 degrees of turning, such as approximately 270 degrees or 180 degrees. The rotatable connection includes threads 108 of the inner shaft 34 that engage threads 110 of the knob 22 of the outer sleeve 30. In one embodiment, the threads 108, 110 are ACME threads. The ACME threads operate as a lock to hold the outer sleeve 30 in the unlocked or locked position thereof by frictional resistance between the threads 108, 110. The frictional resistance between the threads 108, 110 is selected to resist the resilient bias force the arms 44 apply to the sleeve outer sleeve 30 when the outer sleeve 30 is in the locked position and the arms 44 are radially expanded by the drive head 54. To release the driver 10 from the bone screw 24, the surgeon turns the knob 22 to overcome the frictional resistance between the threads 108, 110 and shift the outer sleeve 30 back up along the inner shaft 34.

Regarding FIGS. 1 and 3, by turning the knob 22 and outer sleeve 30 in direction 112, the outer sleeve 30 is rotatably advanced in distal direction 114. The locking portions 80 form a radially enlarged flange portion 120 that is segmented by gaps 122. As the outer sleeve 30 is shifted in distal direction 114, the locking portions 80 of the arms 44 have inner ramp surfaces 116 (see FIG. 5) that engage the ramp surface 66 of the drive head 54. The engagement between the surfaces 116, 66 urges the locking portions 80 radially outward in direction 124 (see FIG. 3) and expands the gaps 122.

With reference to FIGS. 2 and 4, the inner shaft 34 is received in a through opening 37 of the outer sleeve 30. The handle 12 includes an end cap 130, a grip 132, and a transition collar 134. The inner shaft 34 includes a cylindrical body 136 that is received at least partially in a through opening 140 of the transition collar 134. In one embodiment, the cylindrical body 136 includes an annular stop surface 142 that abuts against a surface 144 of the transition collar 134 to limit axial proximal movement of the inner shaft 34 beyond a predetermined position relative to the transition collar 134. Further, the cylindrical body 136 of the inner shaft 34 has a stop surface 139 that contacts a proximal surface 141 of the outer sleeve 30 to limit proximal shifting of the outer sleeve 30 and provides a hard stop for the unlocked position of the outer sleeve 30.

The inner shaft 34 may be connected to the transition collar 134 and the grip 132 in a number of ways. For example, the inner shaft 34 may include threads 150 that are engaged with threads 152 of the transition collar 134. This threaded connection permits the transition collar 134 and the grip 132 to be disconnected from the inner shaft for cleaning by unthreading the transition collar 134 from the inner shaft 34. Further, the outer sleeve 30 may be removed from the inner shaft 34 for cleaning when the distal end portion 18 is disconnected from the bone screw 24 by turning the outer sleeve 30 in direction 112 to advance the outer sleeve 30 distally in direction 114 until the threads 108, 110 disengage and the outer sleeve 30 may be slid distally in direction 114 off of the inner shaft 34. The outer diameter of the drive head 54 is smaller than the outer diameter of a body portion 39 (see FIG. 2) of the inner shaft 34 so that the sleeve portion 40 may pass distally over the drive head 54. Further, the resilient arms 44 may deflect radially outward in directions 124 (see FIG. 3) to permit the locking portions 80 to shift apart as the locking portions 80 travel along the side surfaces 68 of the drive head 54 and snap back together once axially beyond the drive head 54 as the outer sleeve 30 is advanced off of the inner shaft 34 in distal direction 114.

The grip 132 may be secured to the transition collar 134 by welding or fasteners, as some examples. The grip 132 includes a closed bore 156 that receives a portion of the threads 150 of the inner shaft 34. The end cap 130 may be connected to the grip 132 using adhesive, welding, or fasteners, as some examples. In other embodiments, the end cap 130 may have a one-piece construction with the grip 132. The grip 132 is made of a material that provides ease of handling, such as rubber or neoprene.

Figure 5:
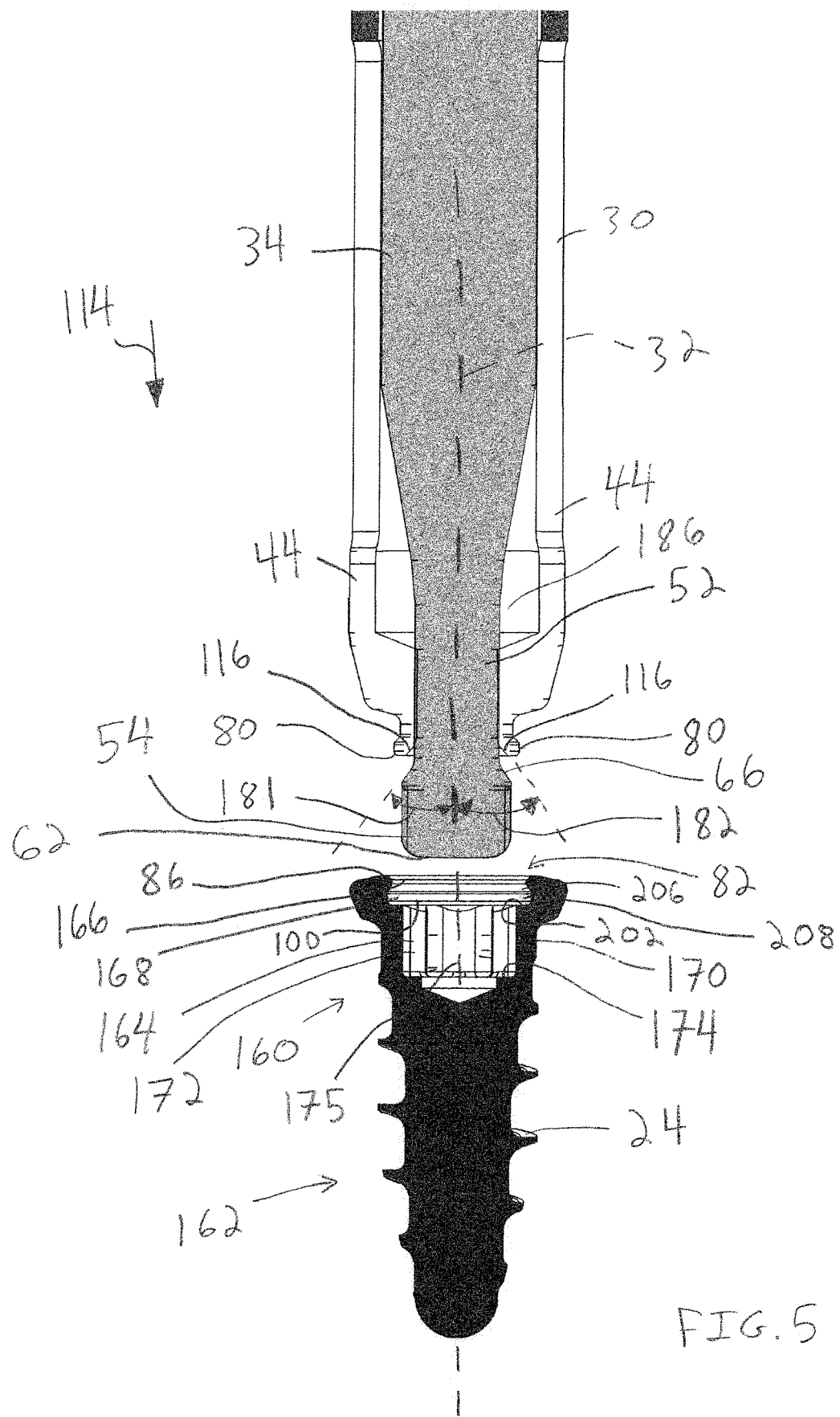
FIG. 5 is a cross-sectional view of the distal end portion of the driver elongate shaft showing the distal end portion in an unlocked configuration with the outer sleeve shifted proximally of the drive head of the inner shaft.

Regarding FIG. 5, the bone screw 24 includes the head portion 160 and a shank portion 162 depending therefrom. The shank portion 162 may include one or more threads that engage the bone. The bone screw 24 includes the drive recess 164 that receives the drive head 54 of the inner shaft 34. The drive recess 164 includes a radially smaller upper securing portion 166 and a radially enlarged lower receiving portion 168. The bone screw 24 includes a side wall 170 having one or more surfaces 172 that engage the axially extending side surfaces 68 of the drive head 54 and form a mating connection therewith. The bone screw 24 further includes a seating surface 174 and the distal surface 62 of the drive head 54 bottoms out against the seating surface 174. The bottoming out of the drive head distal surface 62 against the seating surface 174 of the bone screw 24 provides tactile feedback to the surgeon that the drive head 54 is fully seated in the drive recess 164 of the bone screw 24. Once the drive head 54 is fully seated in the drive recess 164, the surgeon may shift the outer sleeve 30 in the distal direction 114 to the locked position to engage the locking portions 80 with the bone screw 24 and lock the bone screw 24 to the driver 10. In one embodiment, the seating surface 174 extends perpendicularly to a longitudinal axis 175 of the bone screw 24.

Regarding FIG. 5, the inner ramp surface 116 of each of the locking portions 80 extends obliquely at an angle 181 relative to the longitudinal axis 32 of the inner shaft 34.

Likewise, the ramp surface 66 of the drive head 54 extends obliquely at an angle 182 relative to the longitudinal axis 32. In one embodiment, the angle 181 is approximately 35 degrees and the angle 182 is approximately 30 degrees.

In the unlocked configuration of the shaft distal end portion 18, the locking portions 80 are shifted proximally away from the drive head ramp surface 66 along the longitudinal axis 32. The locking portions 80 are received in a recess 186 formed by the smaller diameter neck portion 52. As shown in FIG. 5, the drive head 54 is distal of the locking portions 80 which exposes the drive head 54 and permits a surgeon to readily advance the drive head 54 into the drive recess 164.

Figure 6:
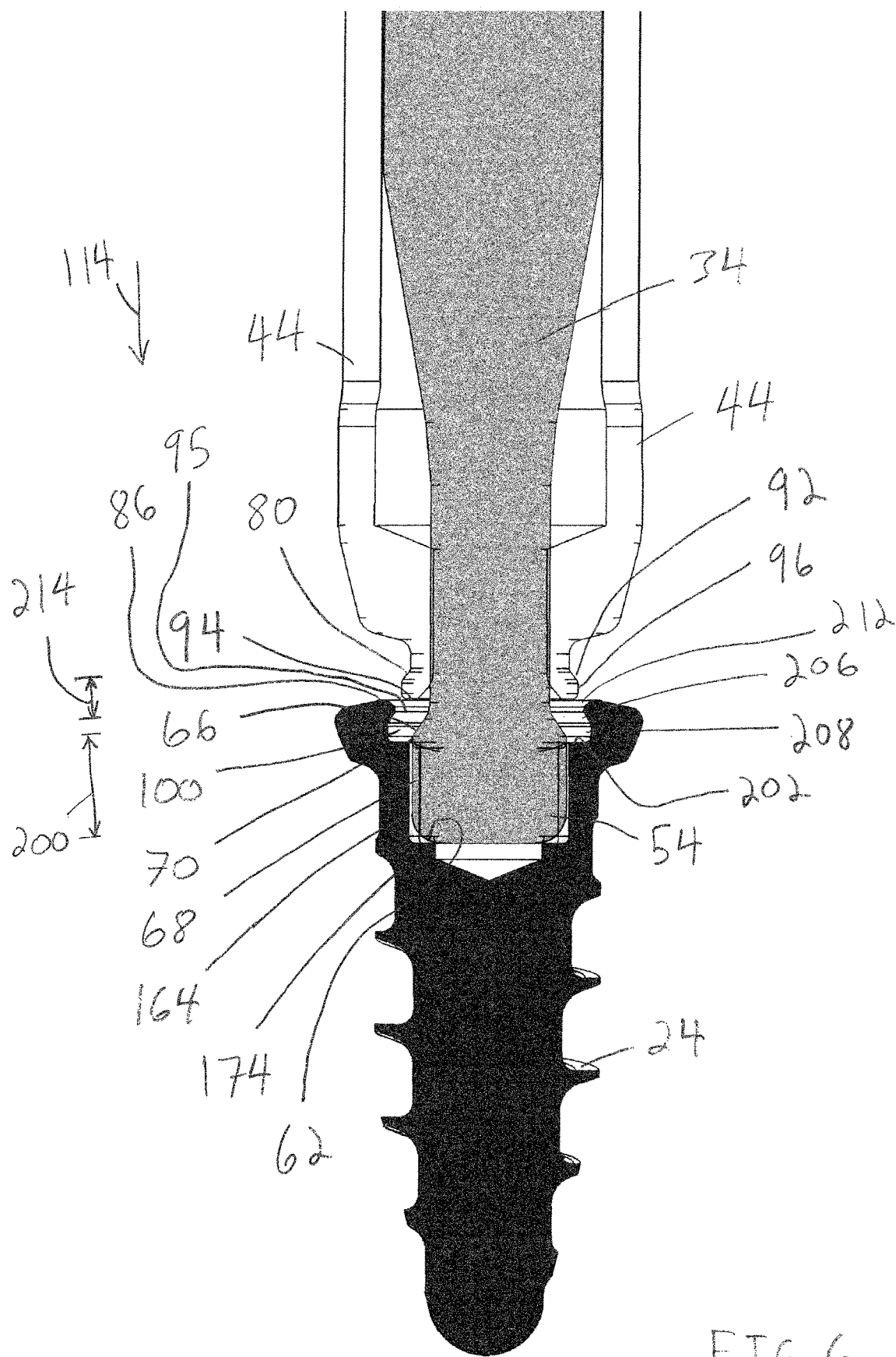
FIG. 6 is a cross-sectional view similar to FIG. 5 showing the drive head seated in a drive recess of the bone screw and locking portions of the outer sleeve resilient arms outside of the drive recess of the bone screw.

Regarding FIG. 6, the drive head 54 has been seated in the drive recess 164 so that the distal surface 62 of the drive head 54 abuts the seating surface 174 of the bone screw 24. The inclined surface 66 of the drive head 54 and the flange 86 of the bone screw 24 cooperate to form a pocket 95 below and sized to receive the locking portions 80. The drive head 54 has an axial height 200 sized to position the ramp surface 66 adjacent to the undercut 100. This positioning permits the locking portions 80 to be shifted outwardly into the undercuts 100 by the ramp surface 66 as the outer sleeve 30 is shifted distally in direction 114. In other words, by having the ramp surface 66 radially aligned with the undercut 100, the ramp surface 66 is positioned at the correct axial position so that the ramp surface 66 may redirect the locking portions 80 radially outward into the engagement with the undercut 100. In one embodiment, the axial height 200 positions the juncture 70 between the ramp surface 66 and the side surfaces 68 of the drive head 54 in radial alignment with a lower redirecting surface 202 of the bone screw 24.

The lower redirecting surface 202 extends radially and operates as an axial stop to limit farther axial movement of the locking portions 80 of the arms 44 in direction 114. The lower redirecting surface 202 provides a surface along which the lower leading surface 94 of the locking portions 80 may shift radially outward along as the surgeon shifts the outer sleeve 30 in distally direction 114 to the locked position thereof. Because the lower redirecting surface 202 limits further distal axial movement of the lower leading surface 94 of the locking portions 80, the locking portions 80 are limited to radially outward movement along the redirecting surface 202 as the outer sleeve 30 is shifted in a distal direction 114.

The radially outward shifting of the locking portions 80 tightly locks the upper locking surface 92 of the locking portions 80 against an upper locking surface 206 of the undercut 100 and urges the axial intermediate surface 96 of the locking portion 80 tightly against an axially extending intermediate surface 208 of the bone screw 24. The upper locking surface 92 may have an incline that matches an incline of the upper locking surface 206. The axial intermediate surface 96 has an axial extent and orientation that matches the intermediate surface 208. Further, the lower leading surface 94 has a shape, e.g., flat, that matches the shape of the redirecting surface 202. The mating profile of the surfaces 92, 206; 96, 208; and 94, 202 removes any gaps between the locking portions 80 and the undercut 100 which keeps the longitudinal axis 175 of the bone screw 24 coaxial with the longitudinal axis 32 of the inner shaft 34 and inhibits toggling of the bone screw 24. Further, the taper of the upper locking surface 92 and the upper locking surface 206 directs the locking portions 80 into a predetermined axial position in the undercuts 100 wherein the axial intermediate surface 96 and intermediate surface 208 are axially aligned and evenly abut once the locking portions 80 are fully expanded. The tapered upper locking surface 92 and upper locking surface 206 thereby assist in reliably forming the mating engagement between the locking portions 80 and the bone screw 24 each time the driver 10 is connected to a bone screw 24.

Regarding FIG. 6, the locking portions 80 of the arms 44 have an axial separation 214 from the drive head 54 when the outer sleeve 30 is in the unlocked position. The bone screw 24 may include an upper, tapered leading surface 212 of the flange 86 extending about the drive recess 164. The upper, tapered leading surface 212 may contact the locking portions 80 as the outer sleeve 30 is shifted from the unlocked position to the locked position and direct the locking portions 80 into the drive recess 164.

Figure 7:
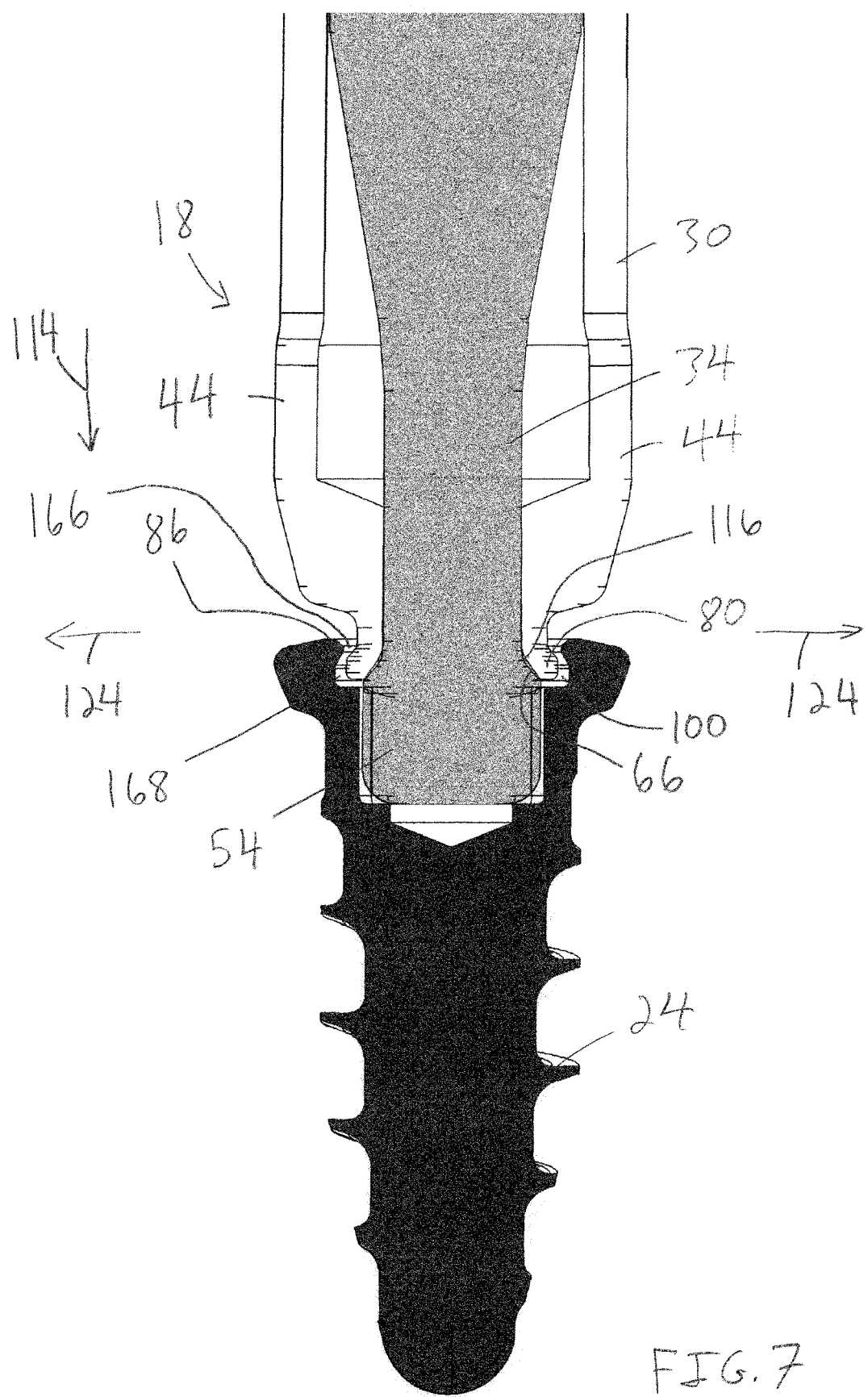
FIG. 7 is a view similar to FIG. 6 showing the outer sleeve shifted distally so that inner surfaces of the resilient arm locking portions engage the proximal ramp surface of the drive head and begin shifting radially outward.

Regarding FIG. 7, the shaft distal end portion 18 is shown in an intermediate configuration wherein the outer sleeve 30 has been shifted distally in direction 114 so that the inner ramp surfaces 116 of the locking portions 80 begin to engage the ramp surface 66 of the drive head 54. The initial engagement has started to urge the locking portions 80 apart in radial directions 124 into the undercut 100 of the bone screw 24.

Regarding FIG. 8, the outer sleeve 30 has been shifted distally in direction 114 to the locked position which engages the locking portions 80 in the undercut 100 and fixes the bone screw 24 to the driver 10. The upper locking surfaces 92 of the locking portions 80 are pressed against the upper locking surface 206 of the undercut 100 and the axial intermediate surfaces 96 of the locking portions 80 are tightly engaged in the radial direction with the axial extending intermediate surface 208 of the undercut 100. The tight, mating engagement of the locking portions 80 and the undercut 100 resists toggling of the bone screw 24 and keeps the bone screw 24 fixed on the drive head 54. Further, the lower leading surface 94 is pressed axially against the lower redirecting surface 202 of the bone screw 24. The flange 86 defines an inner diameter 230 of the drive recess 164. With the locking portions 80 expanded, the locking portions 80 have an effective outer diameter 232 that is larger than the inner diameter 230 of the flange 86. This forms an overlapping relationship of the flange 86 and the locking portions 80 along the longitudinal axis 32 that resists axial separation of the bone screw 24 from the inner shaft 34.

With the bone screw 24 connected to the shaft distal end 18 as shown in FIG. 8, the surgeon may use the handle 12 to maneuver the bone screw 24 along a desired path into a bone plate through opening and into a hole formed in a bone. The surgeon may then turn the handle 12 and the rigid connection between the handle 12 and the inner shaft 34 causes turning of the bone screw 24 and driving of the bone screw 24 into the bone. Once the head portion 160 of the bone screw 24 has been seated in the through opening of the bone plate, the surgeon may reconfigure the shaft distal end portion 18 to the unlocked configuration to disconnect the driver 10 from the bone screw 24. To do this, the surgeon turns the knob 22 in direction 113 (see FIG. 1) which shifts the outer sleeve 30 proximally in direction 115 back up along the inner shaft 34. As the outer sleeve 30 shifts in direction 115, the resiliency of the arms 44 biases the locking portions 80 radially inward in directions 240 (see FIG. 8) and constricts the locking portions 80 together as they are shifted up into the recess 186 formed by the neck portion 52. Once the locking portions 80 have been shifted in direction 115 out of the drive recess 164, the surgeon may then withdraw the drive head 54 in direction 115 outward from the drive recess 164 of the bone screw 24. The surgeon may then connect the driver 10 to the next bone screw 24 and use the driver 10 to drive the next bone screw 23 into the through opening of the bone plate and the underlying bone.

While there have been illustrated and described particular embodiments of the present invention, it will be appreciated that numerous changes and modifications will occur to those skilled in the art, and it is intended for the present invention to cover all those changes and modifications which fall within the scope of the appended claims. For example, the driver may be utilized with a bone anchor other than a bone screw. Further, it is intended that the phrase "at least one of" as used herein be interpreted in the disjunctive sense. For example, the phrase "at least one of A and B" is intended to encompass A, B, or both A and B.

What is claimed is:

1. A bone screw driving system comprising:
   a bone screw having a drive recess and a seating surface of the drive recess;
   a driver including an elongate shaft assembly having a proximal end portion, a distal end portion configured to connect to the bone screw, and a longitudinal axis extending therebetween;
   an inner drive member of the distal end portion of the driver elongate shaft assembly configured to extend into the drive recess of the bone screw;
   a distal surface of the inner drive member configured to seat against the seating surface of the drive recess;
   an outer expansion locking member of the distal end portion of the driver elongate shaft assembly shiftable along the longitudinal axis relative to the inner drive member;
   the outer expansion locking member having an initial configuration wherein the outer expansion locking member is proximal of the inner drive member distal surface and the inner drive member protrudes distally of the outer expansion locking member which permits the inner drive member to be advanced into the drive recess of the bone screw;
   the outer expansion locking member configured to be advanced into the drive recess with the outer expansion locking member in the initial configuration thereof and the inner drive member protruding distally of the outer expansion locking member; and
   the outer expansion locking member having an expanded configuration wherein the outer expansion member is shifted distally from the initial configuration while remaining proximal of the inner drive distal surface and the inner drive member protrudes distally of the outer expansion locking member, the outer expansion locking member in the expanded configuration thereof extending laterally outward of the inner drive member to engage the bone screw and fix the bone screw to the distal end portion of the driver elongate shaft assembly.

2. The bone screw driving system of claim 1 wherein the bone screw drive recess includes an undercut and the outer expansion locking member extends into the undercut with the outer expansion locking member in the expanded configuration thereof.

3. The bone screw driving system of claim 2 wherein the outer expansion locking member includes locking portions of a plurality of resilient arms of the elongate shaft assembly distal end portion, the locking portions configured to fit into the undercut with the outer expansion locking member in the expanded configuration thereof.

4. The bone screw driving system of claim 1 wherein the drive recess of the bone screw includes a proximal, smaller diameter portion and a distal, larger diameter portion; and
   wherein the outer expansion locking member includes at least a portion thereof received in the lower, larger diameter portion with the outer expansion locking member in the expanded configuration and outside of the lower, larger diameter portion with the outer expansion member in the initial configuration.

5. The bone screw driving system of claim 1 wherein the inner drive member includes a ramp surface and at least one side surface extending intermediate the ramp surface and the distal surface; and
   wherein the outer expansion locking member shifts along the ramp surface of the inner drive member and is urged laterally outward by the ramp surface as the outer expansion locking member is reconfigured between the initial and expanded configurations.

6. The bone screw driving system of claim 5 wherein the ramp surface includes a lower end portion and the bone screw drive recess includes a redirecting surface extending transverse to the longitudinal axis; and
   wherein the inner drive member includes an axial height sized to position the ramp surface lower end portion substantially level with the redirecting surface when the distal surface of the inner drive member is seated against the seating surface of the drive recess.

7. The bone screw driving system of claim 1 wherein the driver elongate shaft assembly includes an outer sleeve portion connected to the outer expansion locking member, the outer sleeve portion and outer expansion locking member connected thereto being shiftable relative to the inner drive member in a proximal distal direction to reconfigure the outer expansion locking member from the initial configuration to the expanded configuration and being shiftable in an opposite, distal proximal direction to reconfigure the outer expansion locking member from the expanded configuration to the initial configuration.

8. The bone screw driving system of claim 1 wherein the screw has a unitary, one-piece construction.

9. The bone screw driving system of claim 1 wherein the bone screw and inner drive member form a pocket extending about the inner drive member to receive the outer expansion locking member with the inner drive member distal surface seated against the drive recess seating surface.

10. The bone screw driving system of claim 1 wherein the drive recess of the bone screw has a first width thereacross; and
    wherein the outer expansion locking member in the initial configuration thereof has a distal end portion with a maximum width that is less than the first width of the drive recess to permit the distal end portion of the outer expansion locking member to be advanced into the drive recess while the inner drive member protrudes distally of the outer expansion locking member.

11. The bone screw driving system of claim 1 wherein the inner drive member has a central longitudinal axis;
    wherein the inner drive member includes a ramp surface inclined relative to the central longitudinal axis, the ramp surface of the inner drive member increasing in distance from the central longitudinal axis as the ramp surface extends distally; and
    wherein the outer expansion locking member includes an inclined surface configured to engage the ramp surface of the inner drive member as the outer expansion locking member shifts distally from the initial configuration to the expanded configuration.

* * * * *